United States Patent [19]

Lavigne et al.

[11] Patent Number: 5,592,947
[45] Date of Patent: Jan. 14, 1997

[54] ALGOMETER WITH PRESSURE INTENSIFICATION RATE ADJUSTING AND CONTROL CAPABILITIES

[75] Inventors: Gilles Lavigne; Léo Tenbokum, both of Québec

[73] Assignee: Universite de Montreal, Montreal, Canada

[21] Appl. No.: 437,700

[22] Filed: May 9, 1995

[51] Int. Cl.$^6$ .................................................. A61B 3/00
[52] U.S. Cl. .................................................. 128/744
[58] Field of Search ......................... 128/737, 739–741, 128/744, 774

[56] References Cited

U.S. PATENT DOCUMENTS

| | | | |
|---|---|---|---|
| 4,387,723 | 6/1983 | Atlee et al. | 128/734 |
| 4,543,957 | 10/1985 | Friedman et al. | 128/630 |
| 4,570,640 | 2/1986 | Barsa | 128/741 |
| 4,641,661 | 2/1987 | Kalarickal | 128/744 |
| 4,711,248 | 12/1987 | Steuer et al. | 128/748 |
| 4,844,091 | 7/1989 | Bellak | 128/744 |
| 5,022,407 | 6/1991 | Horch et al. | 128/739 |
| 5,228,443 | 7/1993 | Tatar | 128/653.2 |
| 5,237,501 | 8/1993 | Gusakov | 364/413.01 |
| 5,533,514 | 7/1996 | Lavigine et al. | 128/744 |

OTHER PUBLICATIONS

"The Management of Pain" Bonica, J. J., Lea & Feliger Linchon, 2nd Edition 1990, p. 582.

"Quantification of Tenderness by Palpation and Use of Pressure Algometers" Jensen, K. Advances in Pain Research and Therapy, 1990, vol. 17, pp. 165 and 170.

"TSA 2001–The new Thermal Sensory Analyzer" Medoc Ltd. Advanced Medical Systems 1992, pp. 1–4.

*Primary Examiner*—Max Hindenburg
*Attorney, Agent, or Firm*— Darby & Darby

[57] ABSTRACT

A pressure algometer comprises a tip for applying pressure to a point of the patient's body, a pressure transducer for sensing the intensity of the pressure applied to the patient's body and for producing a pressure intensity representative signal, and first and second elongate, laterally adjacent display units. A ramp signal is generated to drive the first elongate display unit and displace a first visual signal in a given direction along that first display unit at a predetermined speed. In response to the pressure intensity representative signal increasing in amplitude, a second visual signal is displaced in the given direction along the second display unit. In operation, the rate of intensification of the pressure applied to the point of the patient's body is adjusted to follow, with the second visual signal, the first visual signal displacing in the given direction along the first display unit whereby the rate of intensification of the pressure is controlled by the speed of displacement of the first visual signal along the first elongate display unit.

13 Claims, 2 Drawing Sheets

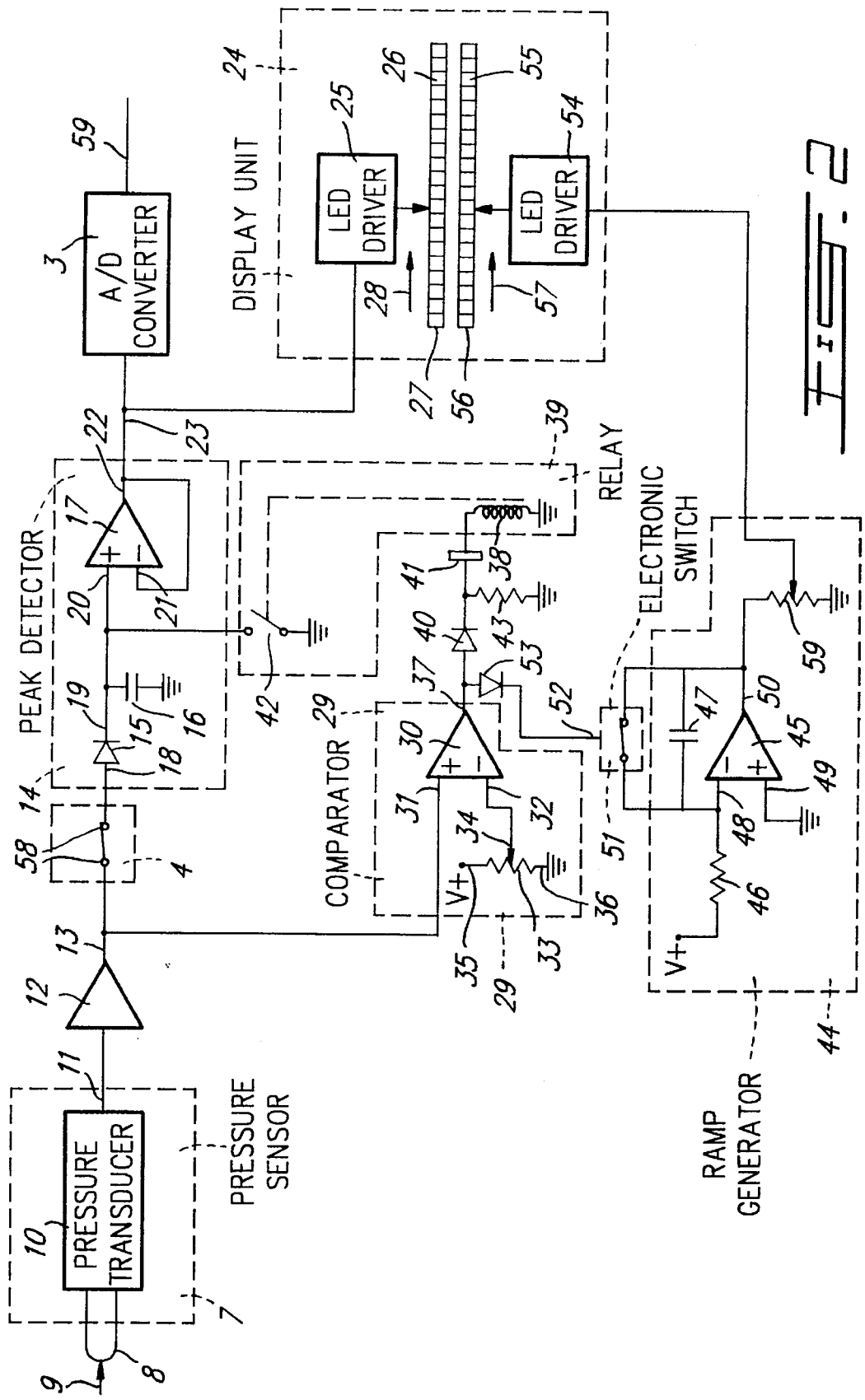

ALGOMETER WITH PRESSURE INTENSIFICATION RATE ADJUSTING AND CONTROL CAPABILITIES

BACKGROUND OF THE INVENTION

1. Field of the Invention

The present invention relates to a method and algometer capable of controlling the rate of intensification of the pressure applied to a point, generally external of a patient's body.

2. Brief Description of the Prior Art

Pain is a subjective, complex phenomenon consisting of (a) a sensorial perception sometimes revealing a potential or real tissular lesion, and (b) the affective response provoked by this sensorial perception. As pain sensation is also psychic, objective evaluation thereof is difficult.

Presently, two main types of pain evaluation are currently used during clinical examination of patients: evaluation of the sensitivity of the affected tissues to pain, and evaluation of the "clinical pain". Evaluation of pain sensitivity is generally carried out by means of palpation of skin or underlying tissues (for example muscles), or by means of other more or less reliable methods. "Clinical pain" is usually evaluated from a verbal report of the patient; these verbal reports are generally unreliable since they depend on the patient's "pain memory" and since chronic pain may widely vary within a same day and from one day to the other.

Also, pressure algometers are available on the market to measure the pressure-pain threshold of a patient at a specific point or at several points of the patient's body. The pressure algometers presently available on the market are designed to apply mechanical pressure to the point(s) of interest of the patient's body and to measure the applied pressure. The patient is instructed to signal, as pressure is applied through the algometer, that the pain threshold has been reached either verbally or by pressing a pushbutton. The pressure measured at this moment is read and taken as the pressure-pain threshold. Using a pressure algometer, only one parameter is measured in contrast to manual palpation where the response and evaluation are more complex.

A prior art pressure algometer is presented in the article of Kai Jensen entitled "Quantification of Tenderness by Palpation and Use of Pressure Algometers" published in Advances in Pain Research and Therapy,. Vol. 17, page 170, edited by James R. Fricton and Essam Awad. Raven Press, Ltd., New York, 1990. This prior art algometer is provided with a display for pressure derivate to allow the user to intensify the pressure at a constant, adjustable rate. A first drawback of the prior art algometer is that the user has to correlate the reading of this display with application of pressure. Another drawback is that the display is installed on a read-out unit separate from the pressure-applying unit.

OBJECT OF THE INVENTION

An object of the present invention is therefore to provide a method and an algometer designed for facilitating intensification of the applied pressure at a constant adjustable rate.

SUMMARY OF THE INVENTION

More specifically, in accordance with the present invention, there is provided a pressure algometer comprising:

a pressure applying member for applying to a point of a patient's body a pressure increasing in intensity;

a pressure sensor for sensing the intensity of the pressure applied to the point of the patient's body and for producing a pressure intensity representative signal having an amplitude which increases with the intensity of the pressure applied;

first and second elongate and laterally adjacent display units for producing first and second visual signals to be displaced along the first and second elongate display units, respectively;

a first display unit driving circuit for displacing the first visual signal in a given direction along the first display unit at a predetermined speed; and a second display unit driving circuit responsive to the pressure intensity representative signal increasing in amplitude for displacing the second visual signal in the above mentioned given direction along the second display unit.

In operation, the pressure applied to the point of the patient's body is intensified at a rate adjusted to follow, with the second visual signal, the first visual signal displacing in the given direction along the first display unit whereby the rate of intensification of the pressure is controlled by the speed of displacement of the first visual signal along the first elongate display unit.

Accordingly, to intensify the applied pressure at a constant rate, the user has only to increase pressure so as to follow the first visual signal with the second visual signal. It is both easy and efficient.

Preferably, the first and second display units comprise first and second, generally parallel and laterally adjacent bar graph displays, respectively.

Also in accordance with the present invention, there is provided a method of controlling the rate of intensification of pressure applied to a point of a patient's body by means of a pressure algometer comprising (a) a pressure applying member for applying pressure to the point of the patient's body, (b) a pressure sensor for sensing the intensity of the pressure applied to this point of the patient's body and for producing a pressure intensity representative signal having an amplitude which increases with the intensity of the pressure applied, and (c) first and second elongate and laterally adjacent display units. The method comprises the steps of:

displacing a first visual signal in a given direction along the first display unit at a predetermined speed;

in response to the pressure intensity representative signal increasing in amplitude, displacing a second visual signal in the given direction along the second display unit; and adjusting the rate of intensification of the pressure applied to the point of the patient's body to follow, with the second visual signal, the first visual signal displacing in the given direction along the first display unit whereby the rate of intensification of the pressure is controlled by the speed of displacement of the first visual signal along the first elongate display unit.

In accordance with preferred embodiments of the method according to the invention:

—it further comprises the step of adjusting the speed of displacement of the first visual signal along the first display unit;

—the step of displacing the second visual signal comprises (a) amplifying the pressure intensity representative signal, (b) detecting the peak amplitude of the amplified pressure intensity representative signal, and (c) driving the second display unit in response to the peak amplitude to displace the second visual signal along that second display unit; and —the method further comprises the step of retaining the peak amplitude of the amplified pressure intensity representative signal when the pressure applied to the point of the patient's body is released.

The objects, advantages and other features of the present invention will become more apparent upon reading of the following non restrictive description of a preferred embodiment thereof, given by way of example only with reference to the accompanying drawings.

BRIEF DESCRIPTION OF THE DRAWINGS

In the appended drawings:

FIG. 2 is a schematic diagram of the electronic circuit of the pressure algometer of the apparatus of FIG. 1, for determining sensitivity to pain caused by pressure.

DETAILED DESCRIPTION OF THE PREFERRED EMBODIMENT

Figure 1:
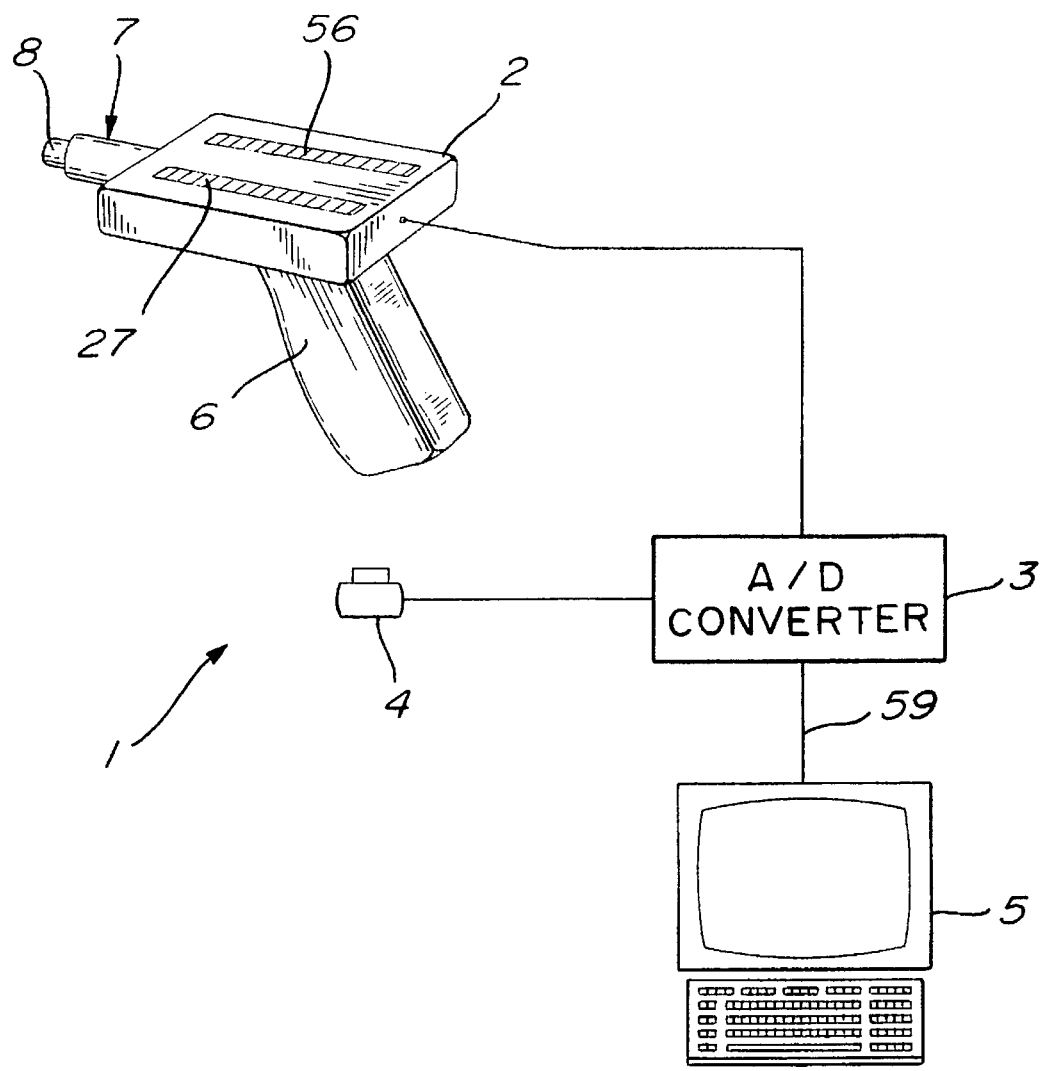
FIG. 1 is a block diagram of an apparatus for determining sensitivity to pain caused by pressure, comprising a pressure algometer in accordance with the present invention, a visual analogue scale (VAS), an analog-to-digital (A/D) converter, a stop pushbutton and a computer.

The apparatus for determining sensitivity to pain caused by pressure in accordance with the present invention is generally identified by the reference 1 in the appended drawings.

As illustrated in FIG. 1, the apparatus 1 for determining sensitivity to pain caused by pressure comprises a pressure algometer 2, an analog-to-digital (A/D) converter 3, a stop pushbutton 4, and a computer 5.

A pressure algometer is an instrument for measuring, through an application of pressure, skin pain and/or pain related to underlying tissues such as the muscles and articulations.

Referring to FIGS. 1 and 2, the pressure algometer 2 comprises a handle 6 to be grasped by the user's hand, a pressure sensor 7 and a tip 8. In operation, the user grasps the handle 6 with one of his hands to apply the tip 8 to the point of interest, generally external of the patient's body (not shown). Pressure is then applied to this point of the patient's body by means of the tip 8. This obviously produces a corresponding pressure 9 (FIG. 2) on the tip 8 of the pressure algometer 2. Pressure 9 is mechanically transmitted through the tip 8 to the pressure sensor 7 including for example a pressure transducer 10 such as a strain gauge. In response to the pressure 9, the pressure transducer 10 produces an electric output signal 11 whose amplitude is proportional to the pressure 9 and therefore to the pressure applied to the point of interest of the patient's body.

The electric signal 11 from the output of the pressure transducer 10 is supplied to an amplifier 12 and the amplified signal 13 at the output of the amplifier 12 is supplied to a peak detector 14 through the stop pushbutton 4. The peak detector 14 comprises a diode 15, a capacitor 16 and an operational amplifier 17.

The diode 15 comprises an anode 18 connected to the output of the amplifier 12 through the stop pushbutton 4, and a cathode 19 connected to the non-inverting input 20 of the operational amplifier 17. The capacitor 16 is connected between the non-inverting input 20 of the operational amplifier 17 and the ground. The inverting input 21 and the output 22 of the operational amplifier 17 are interconnected.

In operation, the amplified signal 13 from the output of the amplifier 12 is supplied to the capacitor 16 through the stop pushbutton 4 and the diode 15. The function of the capacitor 16 is to store the peak amplitude of the amplified signal 13. This peak amplitude is supplied to the output 22 of the operational amplifier 17 (see signal 23 in FIG. 2). Very low current is drained from the capacitor 16 by the operational amplifier 17 for that purpose.

The signal 23 on the output 22 of the operational amplifier 17 is supplied to the A/D converter 3 and to a display unit 24 of the pressure algometer 2. Display unit 24 comprises a LED (light-emitting diode) driver 25 receiving the signal 23 to supply a series 27 of LEDs such as 26. The LEDs 26 are energized from one end of the series 27 and the number of LEDs 26 energized is proportional to the amplitude of the signal 23. In response to a signal 23 varying from a given lower amplitude to a given higher amplitude, the driver 25 will successively energize the LEDs 26 one by one from one end of the series 27 to the other end thereof (for example from left to right in FIG. 2) to give the illusion of a illuminated line lengthening in direction 28. Therefore, the LED driver 25 forms with the series 27 of LEDs 26 a bar-graph display presenting an illuminated line whose length varies in proportion to the amplitude of the signal 23. It is believed to be within the knowledge of one of ordinary skill in the art to construct such well known bar-graph display.

The amplified signal 13 is also supplied to a comparator 29 consisting of an operational amplifier 30 having its non-inverting input 31 connected to the output of the amplifier 12. A threshold DC (direct current) voltage is applied to the inverting input 32 of the operational amplifier 30 by means of a voltage divider formed of a potentiometer 33 having a movable contact 34 connected to the inverting input 32, a first end terminal 35 supplied with a DC voltage $V^+$, and a second end terminal 36 which is grounded. When the amplitude of the amplified signal 13 is lower than the amplitude of the threshold voltage applied to the inverting input 32, the output 37 of the operational amplifier 30 is low. On the contrary, when the amplitude of the signal 13 is higher than the amplitude of the threshold voltage applied to the inverting input 32, the output 37 of the operational amplifier 30 is high.

When the output 37 of the operational amplifier 30 passes from a low to a high level, the high level voltage on the output 37 supplies the coil 38 of a relay 39 through a diode 40 and an electrolytic capacitor 41. Direct current is supplied to the coil 38 as long as the capacitor 41 is not completely charged. Direct current is therefore momentarily supplied to the coil 38 to momentarily close a pair of normally open contact 42 of the relay 39. The pair of contacts 42 are connected in parallel with the capacitor 16 of the peak detector 14, whereby closure of the pair of contacts 42 discharges the capacitor 16 to thereby reset the peak detector 14. The capacitance value of the electrolytic capacitor 41 if selected to close the pair of contacts 42 during a period of time sufficient long to discharge the capacitor 16 but sufficiently short not to disturb operation of the pressure algometer 2 as described hereinafter.

When the output 37 of the operational amplifier 30 subsequently passes from a high to a low level, the electrolytic capacitor 41 discharges into a resistor 43 connected between the positive terminal of the capacitor 41 and the ground.

The amplitude of the threshold voltage applied by the potentiometer 33 to the inverting input 32 of the operational amplifier 30 is so selected that each time the tip 8 of the pressure sensor 7 is touched by the user, the output 37 of the operational amplifier 30 passes from a low to a high level to momentarily supply the coil 38 of the relay 39 and momentarily close the pair of contacts 42 to thereby discharge the capacitor 16 and reset the peak detector 14.

The pressure algometer 2 further comprises a ramp generator 44. Ramp generator 44 comprises an operational amplifier 45, a resistor 46 and a capacitor 47. The operational amplifier 45 has a non-inverting input 49 which is grounded, and an inverting input 48 and an output 50 interconnected by means of the capacitor 47. The DC voltage $V^+$ is applied to the inverting input 48 through the resistor 46.

An electronic switch 51 is connected in parallel with the capacitor 47 of the ramp generator 44 and is controlled by the output of the comparator 29. More specifically, the voltage on the output 37 of the operational amplifier 30 is supplied to a control input 52 of the electronic switch 51 through a diode 53. In response to a low level signal on the output 37 of the operational amplifier 30 the electronic switch 51 is closed to discharge the capacitor 47 and reset the ramp generator 44.

In response to a high level signal on the output 37 of the operational amplifier 30, the electronic switch 51 opens. Then, the direct current produced by the voltage $V^+$ and flowing through the resistor 46 toward the inverting input 48 causes the operational amplifier 45 to produce a direct current flowing through the capacitor 47 from the output 50 toward the inverting input 48 to charge the capacitor 47. As the capacitor 47 charges, the amplitude of the signal on the output 50 of the operational amplifier gradually increases to produce on this output 50 a ramp signal.

The ramp signal from the output 50 of the operational amplifier 45 is supplied to a LED driver 54 of the display unit 24 of the pressure algometer 2. LED driver 54 receives the ramp signal from the output 50 of the operational amplifier 45 to successively energize one by one (from left to right in FIG. 2) the LEDs such as 55 of a second series 56 of LEDs, as the amplitude of the ramp signal increases to give the illusion of a luminous line lengthening in direction 57. Again, the LED driver 54 forms with the series 56 of LEDs 55 a bar-graph display presenting an illuminated line whose length varies in proportion to the amplitude of the ramp signal. As can be seen in FIG. 1, the series 27 and 56 of LEDs are mounted laterally adjacent to each other.

A potentiometer 59 can be interposed between the output 50 of the operational amplifier 45 and the input of the LED driver 54 to adjust the slope of the ramp signal and accordingly the speed of lengthening of the luminous line.

Of course, it is within the scope of the present invention to replace the LED bar-graph displays by LCD (liquid crystal display) bar-graphs, as well as to use other available technologies to move a visual signal along an elongate display unit.

Operation of the pressure algometer 2 will now be described.

Initially, no pressure 9 is applied to the tip 8 of the algometer 2, so that the pressure transducer 10 produces no signal and the amplitude of the signal 13 at the output of the amplifier 12 is substantially equal to zero. Then, the output of the comparator 29 is low whereby the coil 38 of the relay 39 is not energized and the pair of normally-open contacts 42 are open, and whereby the electronic switch 51 is closed and the capacitor 47 discharged to reset the ramp generator 44.

To operate the pressure algometer 2, the handle 6 (FIG. 1) is first grasped by the user's hand and a slight pressure is applied to the point of interest of the patient's body by means of the tip 8. The corresponding pressure 9 applied to the tip 8 is detected by the pressure transducer 10 which produces a signal 11 having an amplitude proportional to the level of the pressure 9, and amplified through the amplifier 12 to produce the amplified signal 13.

As the amplified signal 13 reaches an amplitude higher than the threshold voltage applied to the inverting input 32 by means of the potentiometer 33, the output 37 of the operational amplifier 30 passes from a low to a high level. The coil 38 of the relay 39 is then momentarily energized to close the pairs of normally open contacts 42 to discharge the capacitor 16 and thereby reset the peak detector 14. In response to the high level signal on the output 37 of the operational amplifier 30, the electronic switch 51 is also opened to enable charging of the capacitor 47 and therefore the generator 44 to produce the ramp signal.

As it is explained in the foregoing description, the driver 54 of the display unit 24 is responsive to the ramp signal on the output 50 of the operational amplifier 45 to successively energize the LEDs 55 one by one from one end of the series 56 to the other end thereof and give the illusion of an illuminated line (visual signal) lengthening in direction 57 at a predetermined speed adjustable through the potentiometer 59.

In the meantime, the amplified signal 13 is supplied to the capacitor 16 through the stop pushbutton 4 and the diode 15. The capacitor 16 stores the peak amplitude of the signal 13, which peak amplitude is supplied to the output 22 of the operational amplifier 17 and therefore to the LED driver 25.

The rate of intensification of the pressure applied to the point of interest of the patient's body by means of the tip 8 is so adjusted that the illuminated line (visual signal) formed by the series 27 of LEDs 26 and lengthening in direction 28 follows the illuminated line formed by the series 56 of LEDs 55 and lengthening in direction 57. Therefore, the rate of intensification of the pressure applied to the point of interest of the patient's body is determined by the slope of the ramp signal produced by the ramp generator 44 and controlling the speed of lengthening of the illuminated line (visual signal) formed by the series 56 of LEDs 55. Of course, the rate of intensification of the pressure can be adjusted by modifying the slope of the ramp signal by means of the potentiometer 59.

Accordingly, the rate of intensification of the pressure is substantially the same at each test whereby the parameters of stimulation and the conditions in which the readings are taken are controlled. Better comparison of the pressure-pain thresholds read on the same point of interest of a particular patient's body and obtained at different moments (distant in time) is therefore enabled to follow the evolution of the patient's condition in time. Evaluation of pain becomes more accurate, objective and reproducible (electronic measurement, intensity of the pressure stimuli is controlled, human errors are reduced).

As pressure is applied to the point of interest of the patient's body through the tip 8 of the algometer 2, the patient will feel pain. The patient is then holding the stop pushbutton 4 and he is instructed to signal that the pain threshold has been reached by depressing the stop pushbutton 4. The pressure at this moment constitutes the pressure-pain threshold. Following depression of the stop pushbutton 4, the contacts 58 thereof open to isolate the output of the amplifier 12 from the capacitor 16. The peak amplitude of the signal 13 recorded across the capacitor 16 at the instant of opening of the contacts 58 is retained by the capacitor 16 and supplied to the A/D converter 3 through the operational amplifier 17. The A/D converter 3 converts this analog signal to digital form and stores this digital signal until it is read by the computer 5 (FIG. 1) for further processing thereof.

When the pressure applied by the tip 8 is released, the output 37 of the operational amplifier 30 (see comparator 29) passes from a high level to a low level. The low level signal on the output 37 closes the electronic switch 51 to thereby discharge the capacitor 47 and reset the ramp generator 44. The low level signal on the output 37 of the operational amplifier 30 also enables the capacitor 41 to discharge through a resistor 43 mounted between the cathode of the diode 40 and the ground. The resistance value of the resistor 43 is sufficiently high so that discharge of the capacitor 41 produces a current through the coil 38 of the relay 39 insufficient to close of the pair of contacts 42.

To subsequently reset the peak detector 14, the user has only to touch the tip 8 of the algometer 2 to generate on the output 37 of the operational amplifier 30 a high level signal to momentarily supply the coil 38 of the relay 39 as described in the foregoing description. This closes the pair of contacts 42 to discharge the capacitor 16 and reset the peak detector 14.

The apparatus for determining sensitivity to pain caused by pressure as described in the foregoing description is susceptible of being used by many professionals including orthopaedists, physiotherapeutic professionals, physiologists, dentists, rheumatologists, general physicians, neurologists, psychologists, as well as organisms such as private insurance companies, etc.

The patients will comprise the victims of traumatisms or pathologies on which the efficiency of pharmacological, surgical, physiological, psychological, etc. therapies is studied, and the patients suffering pain following an accident, arthritis, fibromyalgy, dyskinesis, neuropathy, a neurological traumatism, a tension cephaly, etc.

Although the present invention has been described hereinabove by way of a preferred embodiment thereof, this embodiment can be modified at will, within the scope of the appended claims, without departing from the spirit and nature of the subject invention.

What is claimed is:

1. A pressure algometer comprising:

a pressure applying member for applying to a point of a patient's body a pressure increasing in intensity;

a pressure sensor for sensing the intensity of the pressure applied to said point of the patient's body and for producing a pressure intensity representative signal having an amplitude which increases with the intensity of the pressure applied;

first and second elongate and laterally adjacent display units for producing first and second visual signals to be displaced along the first and second elongate display units, respectively;

a first display unit driving circuit for displacing the first visual signal in a given direction along the first display unit at a predetermined speed;

a second display unit driving circuit responsive to the pressure intensity representative signal increasing in amplitude for displacing the second visual signal in said given direction along the second display unit;

wherein, in operation, the pressure applied to said point of the patient's body is intensified at a rate adjusted to follow, with the second visual signal, the first visual signal displacing in said given direction along the first display unit whereby the rate of intensification of the pressure is controlled by the speed of displacement of the first visual signal along the first elongate display unit.

2. The pressure algometer of claim 1, wherein said first and second display units comprise first and second, generally parallel and laterally adjacent bar graph displays, respectively.

3. The pressure algometer of claim 1, in which said first display unit driving circuit comprises a ramp generator for generating a ramp signal and a driver responsive to said ramp signal for displacing the first visual signal in said given direction along the first display unit at a predetermined speed.

4. The pressure algometer of claim 3, in which said ramp generator comprises a potentiometer for adjusting the slope of said ramp signal applied to said driver and therefore the speed of displacement of the first visual signal along the first display unit.

5. The pressure algometer of claim 1, comprising means for adjusting the speed of displacement of the first visual signal along the first display unit.

6. The pressure algometer of claim 3, comprising means for detecting the amplitude of the pressure intensity representative signal and for activating the ramp generator when the amplitude of the pressure intensity representative signal oversteps a predetermined threshold.

7. The pressure algometer of claim 1, in which said second display unit driving circuit comprises means for amplifying the pressure intensity representative signal, means for detecting the peak amplitude of the amplified pressure intensity representative signal, and a driver for driving the second display unit in response to said peak amplitude.

8. The pressure algometer of claim 7, in which said peak amplitude detecting means comprises means for retaining the peak amplitude of the amplified pressure intensity representative signal when the pressure applied to said point of the patient's body is released.

9. The pressure algometer of claim 8, comprising means for resetting the peak amplitude detecting means in response to an application of pressure to the pressure applying member subsequent to said release of pressure.

10. A method of controlling the rate of intensification of pressure applied to a point of a patient's body by means of a pressure algometer comprising (a) a pressure applying member for applying pressure to said point of the patient's body, (b) a pressure sensor for sensing the intensity of the pressure applied to said point of the patient's body and for producing a pressure intensity representative signal having an amplitude which increases with the intensity of the pressure applied, and (c) first and second elongate and laterally adjacent display units, said method comprising the steps of:

displacing a first visual signal in a given direction along the first display unit at a predetermined speed;

in response to the pressure intensity representative signal increasing in amplitude, displacing a second visual signal in said given direction along the second display unit; and adjusting the rate of intensification of the pressure applied to said point of the patient's body to follow, with the second visual signal, the first visual signal displacing in said given direction along the first display unit whereby the rate of intensification of the pressure is controlled by the speed of displacement of the first visual signal along the first elongate display unit.

11. A method of controlling the rate of intensification of pressure applied to a point of a patient's body according to claim 10, further comprising the step of adjusting the speed of displacement of the first visual signal along the first display unit.

12. A method of controlling the rate of intensification of pressure applied to a point of a patient's body according to claim 10, in which said step of displacing the second visual signal comprises the steps of:

amplifying the pressure intensity representative signal;

detecting the peak amplitude of the amplified pressure intensity representative signal; and driving the second display unit in response to said peak amplitude to displace the second visual signal along said second display unit.

13. A method of controlling the rate of intensification of pressure applied to a point of a patient's body according to claim 12, further comprising the step of retaining the peak amplitude of the amplified pressure intensity representative signal when the pressure applied to said point of the patient's body is released.

* * * * *